(12) United States Patent
Deshpande et al.

(10) Patent No.: US 9,505,672 B2
(45) Date of Patent: *Nov. 29, 2016

(54) IODINE-BASED CATALYST FOR REDUCTIVE DEHYDROXYLATION OF VICINAL POLYOLS TO OLEFINS

(71) Applicant: Dow Global Technologies LLC, Midland, MI (US)

(72) Inventors: Raj Deshpande, Pune (IN); Paul Davis, Pune (IN); Vandana Pandey, Pune (IN); Nitin Kore, Solapur (IN); John R. Briggs, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 161 days.

This patent is subject to a terminal disclaimer.

(21) Appl. No.: 14/364,693

(22) PCT Filed: Dec. 5, 2012

(86) PCT No.: PCT/US2012/067830
§ 371 (c)(1),
(2) Date: Jun. 12, 2014

(87) PCT Pub. No.: WO2013/090070
PCT Pub. Date: Jun. 20, 2013

(65) Prior Publication Data
US 2014/0357920 A1    Dec. 4, 2014

Related U.S. Application Data

(60) Provisional application No. 61/570,949, filed on Dec. 15, 2011.

(51) Int. Cl.
*C07C 1/22* (2006.01)
*C07C 1/26* (2006.01)
*C07C 1/24* (2006.01)
*B01J 27/08* (2006.01)

(52) U.S. Cl.
CPC ............ *C07C 1/22* (2013.01); *B01J 27/08* (2013.01); *C07C 1/24* (2013.01); *C07C 1/26* (2013.01); *C07C 2527/06* (2013.01); *C07C 2527/08* (2013.01); *C07C 2527/138* (2013.01)

(58) Field of Classification Search
CPC ............ C07C 1/22; C07C 1/26; C07C 1/24; C07C 11/04; C07C 11/06; B01J 27/08
USPC ........................................ 585/639
See application file for complete search history.

(56) References Cited

U.S. PATENT DOCUMENTS 5,516,960 A * 5/1996 Robinson ............... C07C 1/20
568/671
2007/0215484 A1    9/2007  Peterson et al.
2008/0179194 A1    7/2008  Robinson
2008/0216391 A1    9/2008  Cortright et al.
2009/0299109 A1    12/2009 Gruber et al.
2010/0069691 A1    3/2010  Morschbacker
2010/0076233 A1    3/2010  Cortright et al.
2010/0077655 A1    4/2010  Bauldreay et al.

FOREIGN PATENT DOCUMENTS

WO    2008/103480 A2    8/2008

OTHER PUBLICATIONS

Bradbury, "The Mechanism of the Reaction between Glycerol and Hydriodic Acid" Journal of the American Chemical Society 1952 74 (11), 2709-2712.*
Arceo, Chem. Commun., 2009, p. 3357-3359.
Korshak, et al., "High Molecular Weight Compounds, XXVII. Action of hydriodic acid on ethylene glycol and its polyesters," Izvestiya Akademii Nauk SSSR (1950).
Erlenmeyer, Justus Liebigs Annalen der Chemie, "Studies of the process of the action of hydrogen iodide on glycerin," 1866, vol. 139, No. 2, pp. 211-234 (in both German and English).
Verlag, Science of Synthesis, 2009, Vo.1 47b, "Alkenes," pp. 829-832.
Yang, et al., "Selective Reduction of Biomass by Hydriodic Acid and Its In Situ Regeneration from Iodine by Metal/Hydrogen," ChemSusChem, 2012, No. 7, pp. 1218-1222.
E. Arceo, et al., "Rhenium-Catalyzed Didehydroxylation of Vicinal Diols to Alkenes Using a Simple Alcohol as a Reducing Agent," Journal of the American Chemical Society (JACS) Communications, vol. 132-33, p. 11409 (Jul. 29, 2010).
P. Sarmah, et al., "Regioselective Transformation of Allylic, Benzylic and Tertiary Alcohols into the Corresponding Iodides with Aluminum Triiodide: Deoxygenation of Vicinal Diols," Tetrahedron, vol. 45, No. 1-1 (1989), pp. 3569-3574.
N. Barua, et al., "A New Method for Deoxygenation of Vicinal Diols," Tetrahedron Letters, vol. 23, No. 13 (1982), pp. 1365-1366.
J. Ziegler, et al., Inorganic Chemistry, vol. 48 (2008), pp. 9998-10000.
J. Hine, et al., "The Mechanism of the Transformation of Vicinal Dihalides to Olefins by Reaction with Iodide Ion," Journal of the American Chemical Society, vol. 77 (1955), p. 361.
PCT/US2012/067830,; International Search Report & Written Opinion of the International Searching Authority, mailed Apr. 5, 2013.
PCT/ US2012/067830, International Preliminary Report on Patentability, mailed on Mar. 31, 2014.
PCT US2012/067830, Response Written Opinion, filed Oct. 14, 2013.
PCT US2012/067830, 2nd Response Written Opinion, filed Jan. 22, 2014.

\* cited by examiner

*Primary Examiner* — In Suk Bullock
*Assistant Examiner* — Jason Chong
(74) *Attorney, Agent, or Firm* — Dinsmore & Shohl LLP

(57) ABSTRACT

Olefins are produced by the reductive dehydroxylation of vicinal polyols or esters thereof, or a combination thereof, in a liquid reaction medium, under a hydrogen atmosphere, at a temperature from 50° C. to 250° C., in the presence of a halogen-based, preferably iodine-based, catalyst. Examples of the catalyst, which may be included independently or generated in situ, are iodine ($I_2$), hydroiodic acid (HI), iodic acid ($HIO_3$), lithium iodide (LiI), and combinations thereof.

6 Claims, No Drawings

IODINE-BASED CATALYST FOR REDUCTIVE DEHYDROXYLATION OF VICINAL POLYOLS TO OLEFINS

This application is a non-provisional application claiming priority from the U.S. Provisional Patent Application No. 61/570,949, filed on Dec. 15, 2011, entitled "IODINE-BASED CATALYST FOR REDUCTIVE DEHYDROXYLATION OF VICINAL POLYOLS TO OLEFINS," the teachings of which are incorporated by reference herein as if reproduced in full hereinbelow.

This invention relates generally to the field of reductive dehydroxylation of polyols. More particularly, it is a process to accomplish such reductive dehydroxylation of vicinal diols, polyols and their respective esters.

Sugar alcohols include a variety of diols and polyols. Such are frequently encountered in the form of mixtures of these materials, often including, for example, ethylene glycol, propylene glycol, glycerol, sorbitol, a variety of polyols, and diols containing from two to six carbon atoms. While sugar alcohols often represent viable starting materials for a variety of commercially useful products, such as olefins, the difficulty in separating them from one another may make it consequently difficult to control the selectivity to the desired final product or product mix.

Researchers have addressed conversions of alcohol mixtures in many ways. For example, United States Patent Publication (US) 2007/0215484 (Peterson, et al.) relates to a method of making hydrocarbons from polyalcohols (also known as "polyhydric alcohols" or "polyols") and carbohydrates (e.g., monosaccharides such as glucose, disaccharides such as sucrose, starches including polymers of alpha-D-glucose units such as amylase and amylopectin, and fibers such as cellulose-based polysaccharide fibers). The polyalcohols and carbohydrates are combined with hydroiodic acid (HI) in aqueous solution in an electrochemical cell to form the hydrocarbon and elemental iodine ($I_2$). A parallel reaction within the electrochemical cell reduces the $I_2$ to regenerate HI by reducing elemental iodine.

US 2008/0179194 (Robinson) teaches a coupled electrochemical system and method for its use wherein a polyol feed (e.g., biomass polyol containing feed) is reduced in a reducing solution including HI and a metal ion capable of converting (reducing) $I_2$ to HI during polyol reduction to hydrocarbon. Conversion occurs by way of an electrochemical reaction wherein a reduced metal ion selected from vanadium II ion ($V^{2+}$), europium II ion ($Eu^{2+}$) and titanium II ion ($Ti^{2+}$) is oxidized to its oxidized state with conversion back to its reduced state regenerating HI.

US 2010/0076233 (Cortright, et al.) teaches processes and reactor systems for conversion of an oxygenated hydrocarbon, especially a water-soluble oxygenated hydrocarbon, to a paraffin used as a liquid fuel. The teachings include converting a water-soluble oxygenated hydrocarbon to an oxygenate (e.g., an alcohol, furan, ketone, aldehyde, carboxylic acid, diol, triol or another polyol), then dehydrating the oxygenate to an olefin. The deoxygenation catalyst is preferably a heterogeneous catalyst that comprises at least one metal on a catalyst support. The metals include one or more of Cu, Re, Fe, Ru, Ir, Co, Rh, Pt, Pd, Ni, Os, W, Ag and Au. The catalyst may also include one or more of Mn, Cr, Mo, V, Nb, Ta, Ti, Zr, Y, La, Sc, Zn, Cd, Sn, Ge, P, Al, Ga, In and Tl. See also US 2008/0216391 (Cortright, et al.).

US 2009/0299109 (Gruber, et al.) focuses on dehydration of alcohols derived from a renewable material, e.g., by fermentation or chemical conversion of biomass. Dehydration occurs using a heterogeneous or homogeneous acidic catalyst. Illustrative catalysts include an acid treated aluminum oxide catalyst and a sulfonic acid cation exchange catalyst.

Patent Cooperation Treaty Publication (WO) 2008/103480 (Peterson, et al.) relates to conversion of sugars, biomass or both to hydrocarbons, syngas or other compounds. The conversion includes formation of alcohols or carboxylic acids from biomass and subjecting the alcohols, acids or both to decarboxylation (for carboxylic acids) or dehydration (for alcohols) using a metal catalyst, a metal ion catalyst or a base catalyst. Decarboxylation catalysts include bases such as sodium hydroxide, oxidizing agents such as hydrogen peroxide, hydrogen, metal catalysts (e.g., iron or nickel), acid catalysts (e.g., hydrochloric acid, sulfuric acid or dissolved carbon dioxide), or metal ion (e.g., copper) catalysts.

E. Arceo, et al., in "Rhenium-Catalyzed Didehydroxylation of Vicinal Diols to Alkenes Using a Simple Alcohol as a Reducing Agent," *Journal of the American Chemical Society (JACS) Communications*, Vol. 132-33, p. 11409 (29 Jul. 2010), teach use of an alcohol such as 5-nonanol, 3-octanol or 2-octanol to enhance conversion of a vicinal diol such as 1,2-tetradecanediol to an olefin using dirhenium decacarbonyl as a catalyst.

P. Sarmah, et al., in "Regioselective Transformation of Allylic, Benzylic and Tertiary Alcohols into the Corresponding Iodides with Aluminum Triiodide: Deoxygenation of Vicinal Diols," *Tetrahedron*, Vol. 45, No. 1-1 (1989), pp. 3569-3574, teach use of a stoichiometric amount of aluminum triiodide as a catalyst to convert vicinal diols to olefins.

N. Barua, et al., in "A New Method for Deoxygenation of Vicinal Diols," *Tetrahedron Letters*, Vol. 23, No. 13 (1982), pp. 1365-1366, discusses conversion of cis- and trans-vicinal diols into olefins in a one-step reaction using a combination of chlorotrimethylsilane and sodium iodide, with sodium iodide being present in an amount in excess of what stoichiometry would indicate is necessary.

J. Ziegler, et al., in *Inorganic Chemistry*, Vol. 48 (2008), pp. 9998-10000, provides for use of methyltrioxorhenium in catalytic conversion of epoxides and vicinal diols to olefins with $H_2$ as a reductant.

J. Hine, et al., in "The Mechanism of the Transformation of Vicinal Dihalides to Olefins by Reaction with Iodide Ion," *Journal of the American Chemical Society*, Vol. 77 (1955), p. 365, discusses conversion of vicinal dihalides (e.g., 1,2-dibromobutane) to olefins by reaction with a stoichiometric amount of an iodide ion (e.g., that present in a solution of potassium iodide in methanol).

Despite the many approaches to similar or related problems, there remains a need for simple and economical processes to convert vicinal polyols and related compounds to olefins.

In one aspect, this invention provides a process for preparing an olefin, comprising subjecting a material selected from the group consisting of a vicinal polyol, an ester of a vicinal polyol, and combinations thereof, to a reductive dehydroxylation in the presence of a halogen-based catalyst that contains at least one halogen atom per molecule thereof, under conditions including the presence of gaseous hydrogen at a pressure of from 1 pound per square inch gauge (~6.89 kilopascals) to 2000 pound per square inch gauge (~13.79 megapascals), a temperature ranging from 50° C. to 250° C., a liquid reaction medium, and a ratio of moles of the material to moles of the halogen atoms ranging from 1:10 to 100:1; such that an olefin is formed.

A particular feature of the present invention is use of a catalyst that is halogen-based, and preferably iodine-based.

As defined herein, the term "halogen-based-" means that the catalyst contains at least one halogen, preferably iodine, atom and ionizes at least partially in an aqueous solution by losing one proton. It is important to note that the definition of "halogen-based" is applied to the catalyst at the point at which it catalyzes the dehydroxylation of the material. Thus, it may be formed in situ in the liquid reaction medium as or beginning with, for example, an elemental halogen such as elemental iodine ($I_2$), or it may be introduced into the reaction as a halide, for example, an iodide such as pre-prepared HI. Non-limiting examples include iodine ($I_2$), hydroiodic acid (HI), iodic acid ($HIO_3$), lithium iodide (LiI), and combinations thereof. The term "catalyst" is used in the conventionally understood sense, to clarify that the halogen-based catalyst takes part in the reaction but is regenerated thereafter and does not become part of the final product. The halogen-based catalyst is at least partially soluble in the liquid reaction medium.

For example, in one non-limiting embodiment where HI is selected as the iodine-based catalyst, it may be prepared as it is frequently prepared industrially, i.e., via the reaction of $I_2$ with hydrazine, which also yields nitrogen gas, as shown in the following equation.

$$2I_2 + N_2H_4 \rightarrow 4HI + N_2 \quad \text{[Equation 1]}$$

When this reaction is performed in water, the HI must then be separated, via means such as distillation. Alternatively, HI may be distilled from a solution of NaI or another alkali iodide in concentrated hypophosphorous acid. Another way to prepare HI is by bubbling hydrogen sulfide steam through an aqueous solution of iodine, forming the hydroiodic acid (which can then be distilled) and elemental sulfur (which is typically filtered).

$$H_2S + I_2 \rightarrow 2HI + S \quad \text{[Equation 2]}$$

Additionally, HI can be prepared by simply combining $H_2$ and $I_2$. This method is usually employed to generate high purity samples.

$$H_2 + I_2 \rightarrow 2HI \quad \text{[Equation 3]}$$

Those skilled in the art will be able to easily identify process parameters and additional methods to prepare HI and/or other reagents falling within the scope of the invention. It is noted that sulfuric acid will not generally work for preparing HI as it will tend to oxidize the iodide to form elemental iodine.

As used herein the term "material" is used to define the compound being converted by the action of the catalyst in the presence of the gaseous hydrogen under the reductive dehydroxylation conditions. This compound may be any vicinal polyol, an ester of a vicinal polyol, or any combination thereof, provided that the vicinal polyol present or represented in the material has at least 2 carbon atoms, preferably from 2 to 12 carbon atoms, more preferably from 2 to 8 carbon atoms, and most preferably from 2 to 6 carbon atoms. The term vicinal means that the polyol or ester has hydroxyl or ester or combinations of hydroxyl and ester groups on adjacent carbons, and the total number of hydroxyl and ester groups may vary according to the number of backbone carbons. Non-limiting examples of such may include ethylene glycol, propylene glycol, ethylene glycol diacetate, glycerol, glycerol diacetate, glycerol triacetate, and combinations thereof. Mixtures of at least two vicinal polyols, esters of vicinal polyols, or a combination thereof can be selected. Such may be intentionally manufactured or purchased as a starting material, or may be a byproduct of another manufacturing process.

The amounts of the material and the catalyst are desirably proportioned for optimized conversion to the olefin or olefins. Those skilled in the art will be aware without further instruction as to how to determine such proportions, but generally a ratio of moles of material to moles of halogen, preferably iodine, atoms ranging from 1:10 to 100:1 is preferred. More preferred is a molar ratio ranging from 1:1 to 100:1; still more preferably from 4:1 to 27:1; and most preferably from 4:1 to 8:1.

Temperature parameters employed in the invention may vary within a range of from 50° C. to 250° C., but are preferably from 100° C. to 210° C. Those skilled in the art will be aware that certain temperatures may be preferably combined with certain molar ratios of material and catalyst to obtain optimized olefin yield. For example, a temperature of at least 180° C. combined with a molar ratio of material to halogen atom of 6:1 may yield, in some embodiments, especially good yields. Other combinations of temperature and ratio of moles of material to moles of halogen atom may also yield desirable results in terms of conversion of material and selectivity to desired alkenes. For example, with an excess of HI, temperature may be varied especially within the preferred range of 100° C. to 210° C., to obtain a range of selectivity and conversion at a fixed time, e.g., three hours. Processing for a longer time at lower temperature is another embodiment. Those skilled in the art will be aware that alteration of any parameter or combination of parameters may affect yields and selectivities achieved.

In certain particular embodiments the conditions may also include a reaction time, in particular embodiments within a range of from 1 hour to 10 hours. While a time longer than 10 hours may be selected, such may tend to favor formation of byproducts such as those resulting from a reaction of the olefin with one or more of the reactants. Byproduct formation may be more prevalent in a batch reactor than in a continuous process, though either method may be used. Conversely, a time shorter than 1 hour may reduce olefin yield.

Gaseous hydrogen used in the invention, i.e., the reductive atmosphere for the reductive dehydroxylation, may be in essentially pure form, but in alternative embodiments may be in mixtures with, for example, carbon dioxide, carbon monoxide, nitrogen, methane, and any combination of hydrogen with one or more the above. The hydrogen itself may therefore be present in the stream in an amount ranging from 1 weight percent (wt %) to 100 wt %. The hydrogen or mixture including hydrogen is useful in the present invention at a pressure sufficient to promote conversion to the olefin. The pressure is desirably autogenous or may range from 1 psig ~(6.89 KPa) to 2000 psig (~13.79 MPa), and preferably from 50 psig (~344.5 KPa) to 200 psig (~1.38 MPa). When the liquid reaction medium is a carboxylic acid such as acetic acid, esterification of the polyol occurs, liberating water. In many embodiments hydrogen pressures in excess of 2000 psig (~13.79 MPa) provide little or no discernible benefit and may simply increase cost of the process.

The process may generally be accomplished using many of the equipment and overall processing parameter selections that are known to those skilled in the art. According to processing parameters selected, it is necessary to ensure the presence of a liquid reaction medium. Any of the "materials," as defined hereinabove, may function as both the compound to be converted and an additional liquid reaction medium wherein the conversion can most effectively take place. In one embodiment, a carboxylic acid that contains from 2 carbon atoms to 20 carbon atoms, preferably from 8 carbon atoms to 16 carbon atoms, may be selected as a liquid reaction medium. Other organic solvents, such as polyols and dialkyl ethers, may also be selected, and/or water may be used. The organic solvent can also facilitate solubilization of iodine. For instance, an organic solvent such as 1,1,2,2-tetrachloroethane can be used along with acetic acid. Where the material selected for conversion is a polyol, it may be desirable in some non-limiting embodiments for the polyol to be sufficiently miscible in the carboxylic acid that a reaction between the carboxylic acid and the polyol esterifies at least some ester of the polyol. This facilitates the conversion of the polyol to an olefin. In another aspect, the dehydroxylation may be performed using a two phase system, wherein the reactant polyol has a significantly low solubility in one of the phases. This protocol facilitates separation of water formed during the reaction.

It is noteworthy that the inventive process may be accomplished in either one or two steps. If a two step process is desired, the basic reaction may first be conducted, for example, under stochiometric conditions. In this case a relatively low temperature in the range of from 50° C. to 120° C. and a the relatively low (less than 50 psig, ~0.34 MPa) pressure of hydrogen may be effectively employed. This protocol helps to avoid the formation of byproducts. The regeneration of $I_2$ to HI may then be undertaken in a second step at a higher temperature, in the range of from 180° C. to 210° C., and under a similar hydrogen pressure. Notwithstanding the above, those skilled in the art will recognize that alterations of molar ratios of material to iodine atoms, within the scope of the invention, may render different conditions more effective in achieving desired results.

EXAMPLES

General Experimental Procedure

Use a 300 milliliter (mL), High Pressure HASTELLOY™ C-276 Parr reactor with a glass insert as a reaction vessel. Charge 90 milliliters (mL) of acetic acid (S.D. Fine-Chem Ltd.) into the reactor. Add a known amount of ethylene glycol (EG) (S.D. Fine-Chem Ltd.) or ethylene glycol diacetate (EGA, Sigma Aldrich), 1,2-propylene glycol (PG) (Merck) or glycerol (S.D. Fine-Chem Ltd.) (according to the Examples) to the acetic acid. Add 4 mL of a 55% (weight/weight) aqueous solution of hydrogen iodide (HI) (Merck) or 3.73 gram (g) $I_2$ (S.D. Fine-Chem Ltd.) to the reactor, then close the reactor and mount it on a reactor stand. Flush void space within the reactor two times with gaseous nitrogen (200 psig (~1.38 MPa)). Feed $H_2$ into the reactor up to a pressure of 500 psig (~3.45 MPa) and heat reactor contents, with stirring at a rate of 1000 revolutions per minute (rpm) up to a temperature of 210° C. Add sufficient additional $H_2$ to the reactor to increase pressure within the reactor up to 1000 psig (~6.89 MPa). After 45 minutes of reaction time, remove a sample of vapor phase within the reactor using a gas sampling vessel. Analyze the sample via gas chromatography (GC) (Agilent 7890 with two thermal conductivity detectors (TCDs) and one flame ionization detector (FID)). Use a PoraPlot™ Q (Varian™ CP7554) column to separate carbon dioxide ($CO_2$), olefins and alkanes. Use a CP Wax (Varian™ CP7558) column to separate oxygenates and a molecular sieve (Molsieve) (Varian™ CP7539) column to separate hydrogen, nitrogen and lower hydrocarbons. Allow the reaction to continue for 6 hours, intermittently repressurizing the reactor with additional $H_2$ (1000 psig (~6.89 MPa)) to make up for consumption of $H_2$ during the reaction.

Procedure variation for Examples 12, 13 and 14 only: GC analysis of the liquid sample is carried out using an Agilent 7890 gas chromatogram fitted with a split/splitless capillary injector with a split injector liner, tapered, low pressure drop with glass wool and flame ionization detector. The injection volume used is 1 microliter (μL) and the split ratio is 1:20. The GC method uses a combined DB1701 and HP5 GC columns Samples are injected using an Agilent 7683 auto injector.

Procedure Variation for Examples 15-17

Use a 100 mL glass reactor with external heating and vertical condensor. Charge 80 mL of acetic acid (S.D. Fine-Chem Ltd.) into the reactor. Add a known amount of glycerol (S.D. Fine-Chem Ltd.) to the acetic acid. Add 18 mL of a 55% (weight/weight) aqueous solution of hydrogen iodide (HI) (Merck), then close the reactor. Flush void space within the reactor with gaseous $N_2$ (50 mL/min) Heat the reactor with stirring at a rate of 400 revolutions per minute (rpm) up to a temperature of 120° C. and $N_2$ flow of 10 mL/min Analyze the gaseous products by GC at an interval of 21 minutes.

Calculate mole percent (mol %) conversion of material to olefin from vapor phase composition data according to the following equation:

$$\text{mole \%} = \left[ \frac{\frac{\text{vol \%}}{100} \times \frac{\text{total pressure}}{14.7} \times \frac{\text{volume of gas}}{22400}}{\text{moles of material}} \right] \times 100 \quad \text{[Equation 4]}$$

Example 1

Using the above General Experimental Procedure with 0.19 moles of ethylene glycol (EG), 0.029 moles of HI, a temperature of 210° C. and a time of 6 hours, effect a 100% conversion of EG with a product stream selectivity of 96 mole percent (mol %) ethylene, 1 mol % ethane and 3 mol % $CO_2$, each mol % being based upon combined moles of ethylene, ethane and $CO_2$. Liquid phase analysis shows no detectable EG, iodo-species, or acetates or condensed species derived from EG.

Example 2

Replicate Example 1, but substitute 0.019 moles of 1,2-propylene glycol (PG) for the EG, change the number of moles of HI to 0.004 moles, and the time to 3 hours. This Example 2 effects 100% conversion of the PG with a product stream selectivity of 99 mol % propylene, and 1 mol % $CO_2$, each mol % being based upon combined moles of propylene and $CO_2$. Liquid phase analysis shows no detectable PG, iodo-species or acetates or condensed species derived from PG, thereby supporting 100% conversion of PG.

Example 3

Replicate Example 2, but substitute 0.029 moles of glycerol for the PG and increase the time to 5 hours. This Example 3 effects 100% conversion of glycerol with a product stream selectivity of 78 mol % propylene, and 22 mol % $CO_2$, each mol % being based upon combined moles of propylene and $CO_2$. Liquid phase analysis shows no detectable glycerol, iodo-species or acetates or condensed species derived from glycerol, thereby supporting 100% conversion of glycerol.

Example 4

Replicate Example 1, but change the amount of EG to 0.18 mole, substitute 0.015 mole of $I_2$ for the HI and change the time to 14 hours. This Example 4 effects a 100% conversion of EG with a product stream selectivity of 95 mol % ethylene, 3 mol % ethane and 2 mol % $CO_2$, each mol % being based upon total combined moles of ethylene, ethane and $CO_2$.

Example 5

Replicate Example 1, but change the amount of EG to 0.1 mole, the amount of HI to 0.3 mole, the temperature to 100° C. and the time to 5 hours. This Example 5 effects a 73% conversion of EG with a product stream selectivity of 100 mol % ethylene. This Example 5 shows that the inventive process may be carried out at a lower temperature with excess HI, but conversion of EG is thereby reduced.

Example 6

Replicate Example 1, but substitute a mixture of 0.09 mole EG and 0.09 mole PG for the EG, and change the amount of HI to 0.029 mole. This Example 6 effects a 100% conversion of EG with a product stream selectivity of 95 mol % ethylene, 3 mol % ethane and 2 mol % $CO_2$, each mol % being based combined moles of ethylene, ethane and $CO_2$ present in product from the EG portion (50 mole percent) of the mixture, and a 100% conversion of PG with a product stream selectivity of 94 mol % propylene, 3 mol % propane and 3 mol % $CO_2$, each mol % being based upon combined moles of propylene, propane and $CO_2$ present in product from the PG portion of the mixture.

Example 7

Replicate Example 1, but change the amount of EG to 0.82 mole, change the feed to the reactor from pure hydrogen to a mixture of 150 psig (1.03 MPa) $H_2$ and 150 psig (1.03 MPa) CO (replicating synthesis gas), increase the time for reaction to 12.75 hours with a brief interruption when vapor phase concentration within the reactor reaches approximately 33 volume percent (vol %) ethylene to cool reactor contents to 35° C., extract a liquid sample for analysis, and vent gas phase contents before repressurizing the reactor and continuing the reaction as before. This Example 7 effects a 100% conversion of EG with a product stream selectivity of 88 mol % ethylene, and 12 mol % $CO_2$, each mol % being based upon combined moles of ethylene and $CO_2$. This Example 7 shows that one can use an alternate or impure source of hydrogen rather than pure hydrogen.

Example 8

Replicate Example 1, but replace the acetic acid with 0.42 mole of decanoic acid and reduce the time to 3 hours. This Comparative Example A effects an 8% conversion of EG with a product stream selectivity of 96 mol % ethylene, 2 mol % ethane and 2 mol % $CO_2$, each mol % being based upon combined moles of ethylene, ethane and $CO_2$. It is theorized that the reduced activity may be attributable to a reduced rate of generation of HI from $H_2$ and $I_2$ in the decanoic acid.

Example 9

Replicate Example 1, but substitute 12.44 g (0.014 mole of soybean oil (triglyceride esters of glycerol with saturated and unsaturated fatty acids)) for the EG and change the time to 3 hours to effect 100% conversion of the triglyceride esters with a product stream selectivity of 8 mol % propylene, 88 mol % propane and 4 mol % $CO_2$, each mol % being based upon combined moles of propylene, ethane and $CO_2$.

Example 10

Replicate Example 9, but change the amount of HI from 0.029 moles to 0.004 moles and increase the time to 6 hours to effect 100% conversion of the triglyceride esters with a product stream selectivity of 85 mol % propylene, 2 mol % propane and 13 mol % $CO_2$, each mol % being based upon combined moles of propylene, ethane and $CO_2$. A comparison of this Example 10 and Example 2 suggests that, as between the two Examples, the combination of a lower HI concentration, giving a lower polyol to iodide ratio, and a longer reaction time favors selectivity to alkenes versus alkanes.

Example 11

Replicate Example 9, but use EG in an amount of 0.18 moles to 0.03 moles of an aqueous solution of lithium iodide (LiI) and increase the time to 7.5 hours to effect 29% conversion of the EG, with a selectivity of 96% to ethylene and 4% to ethane.

Example 12

Replicate Example 1, but substitute procedure variation in General Experimental Procedure. Also substitute ethylene glycol acetate (EGA, 0.18) for EG, iodine ($I_2$, 0.015 moles) for HI, and carry out the reaction in the presence of $H_2$ (400 psig, ~2.76 megapascals (MPa)) over a period of 6 hours at 210° C. to achieve a conversion of 11% with selectivities of 87% for ethylene, 12% for ethylene, 12% for ethane, and 1% for $CO_2$.

Example 13

Replicate Example 12, but substitute HI (0.33 moles) to achieve a conversion of 23% with selectivities of 98% for ethylene, 1% for ethane and 1% for $CO_2$.

Example 14

Replicate Example 13 but substitute water (0.36 moles) (twice the molar ratio of EGA) to achieve a conversion of 96% with selectivities of 96% for ethylene, 3% for ethane and 1% for $CO_2$.

Example 15

Use procedure of Example 14 for an atmospheric pressure reaction with 0.042 moles of glycerol, 0.13 moles of HI, a temperature of 120° C. and a time of 11 hours. This Example 16 effects 90% conversion of glycerol with a product stream selectivity of 100 mol % propylene. The reaction mixture is then charged into a HASTELLOY™ C-276 reactor and heated at 210° C. for 2 hours under 1000 psig (~6.89 MPa) of $H_2$. Cool the reactor and transfer the contents to a glass reactor. Charge 0.0267 moles of glycerol and continue the reaction as before. After 6 hours of reaction effect 92% conversion with 77, 20, 3 mol % selectivities for propylene, propane and $CO_2$, respectively.

Example 16

Replicate Example 1, but change the amount of EG to 0.20 moles and substitute acetic acid with 0.85 moles of 1,1,2,2-tetrachloroethane. This Example 16 effects 60% conversion of the EG with a product stream selectivity of 62 mol % ethylene, and 38 mol % $CO_2$, each mol % being based upon combined moles of ethylene and $CO_2$.

The invention claimed is:

1. A process for preparing an olefin comprising:
subjecting a material to a reductive dehydroxylation in presence of an iodine-based catalyst, a liquid reaction medium, and 0.1 wt % to 100 wt % gaseous hydrogen to form an olefin;
performing the reductive dehydroxylation under conditions comprising a hydrogen pressure ranging from 1 psig to 2000 psig, a temperature ranging from 50° C. to 250° C., and a ratio of moles of the material to moles of iodine atoms in the iodine-based catalyst ranging from 4:1 to 27:1;
wherein the material is selected from the group consisting of a vicinal polyol, an ester of a vicinal polyol, and combinations thereof; and
wherein the iodine-based catalyst is selected from the group consisting of iodine ($I_2$), hydroiodic acid (HI), lithium iodide (LiI), and combinations thereof.

2. The process of claim 1, wherein the hydrogen pressure is from 50 psig to 500 psig.

3. The process of claim 1, wherein the temperature ranges from 100° C. to 210° C.

4. The process of claim 1, wherein the ratio of moles of the material to moles of the iodine atoms ranges from 4:1 to 8:1.

5. The process of claim 1, wherein the gaseous hydrogen is part of a mixture that further includes at least one additional gas selected from carbon monoxide, carbon dioxide, nitrogen, methane, and combinations thereof.

6. The process of claim 1, wherein the reductive dehydroxylation is conducted as a two-step process comprising a first step and a second step,
wherein the first step comprises a partial dehydroxylation under conditions including a first hydrogen pressure ranging from 1 psig to 50 psig and a first temperature ranging from 50° C. to 120° C., and;
wherein the second step comprises continuing the dehydroxylation from the first step to completion under conditions including a second hydrogen pressure ranging from 1 psig to 50 psig and a second temperature ranging from 180° C. to 210° C.

* * * * *